(12) United States Patent
Hebeisen et al.

(10) Patent No.: US 6,504,025 B2
(45) Date of Patent: Jan. 7, 2003

(54) PROCESS FOR THE PREPARATION OF VINYL-PYRROLIDINONE CEPHALOSPORIN DERIVATIVES

(75) Inventors: Paul Hebeisen, Basel (CH); Hans Hilpert, Reinach (CH); Roland Humm, Riehen (CH)

(73) Assignee: Basilea Pharmaceutica AG, Binningen (CH)

( * ) Notice: Subject to any disclaimer, the term of this patent is extended or adjusted under 35 U.S.C. 154(b) by 0 days.

(21) Appl. No.: 09/860,157

(22) Filed: May 17, 2001

(65) Prior Publication Data

US 2002/0019381 A1 Feb. 14, 2002

(30) Foreign Application Priority Data

May 24, 2000 (EP) .............................. 00111164

(51) Int. Cl.[7] ...................... C07D 501/24; C07D 501/34
(52) U.S. Cl. ....................... 540/222; 540/228
(58) Field of Search ................... 520/222, 228

(56) References Cited

U.S. PATENT DOCUMENTS

| 5,466,811 A | 11/1995 | Alexander |
| 5,672,711 A | 9/1997 | Kim et al. |

FOREIGN PATENT DOCUMENTS

| EP | 0812846 | 12/1997 |
| EP | 0849269 | 6/1998 |
| WO | WO-98/43981 | * 10/1998 |
| WO | WO 99/65920 | 12/1999 |

OTHER PUBLICATIONS

J. Antibiot. (1984) vol. 37(5) pp. 557–571.
Green, T., Protective Groups in Organic Synthesis, Chapter 5, John Wiley & Sons, Inc. (1981) pp. 152–192.
Green, T., Protective Groups in Organic Synthesis, Chapter 7, John Wiley & Sons Inc. (1981) pp. 218–287.
Inokuchi et al J. Org. Chemistry vol. 56, 1991 pp. 2416–2421.

* cited by examiner

*Primary Examiner*—Mark L. Berch
(74) *Attorney, Agent, or Firm*—George W. Johnston; Patricia S. Rocha-Tramaloni; Eileen M. Ebel

(57) ABSTRACT

Disclosed is a process for the preparation of vinyl-pyrrolidinone cephalosporine derivatives of formula

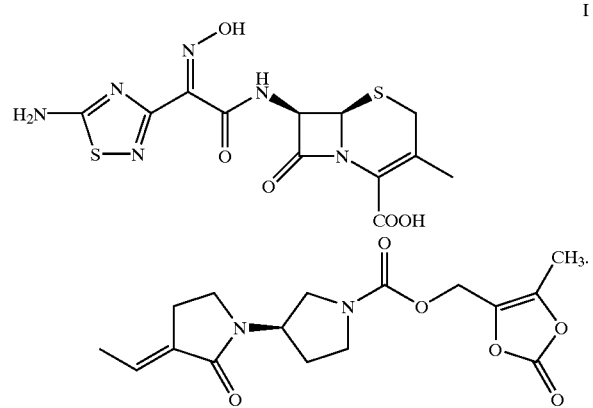

I

Also disclosed are intermediate compounds of formulas

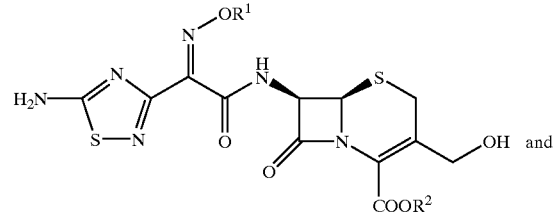

IV and

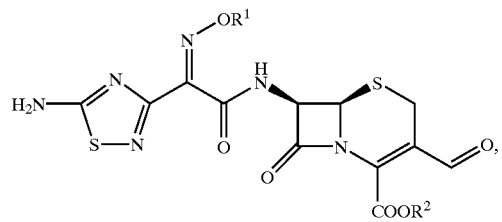

V wherein $R^1$ and $R^2$ are as defined herein.

16 Claims, No Drawings

PROCESS FOR THE PREPARATION OF VINYL-PYRROLIDINONE CEPHALOSPORIN DERIVATIVES

BACKGROUND OF THE INVENTION

The invention relates to a process for the preparation of a vinyl-pyrrolidinone cephalosporine derivative of formula I:

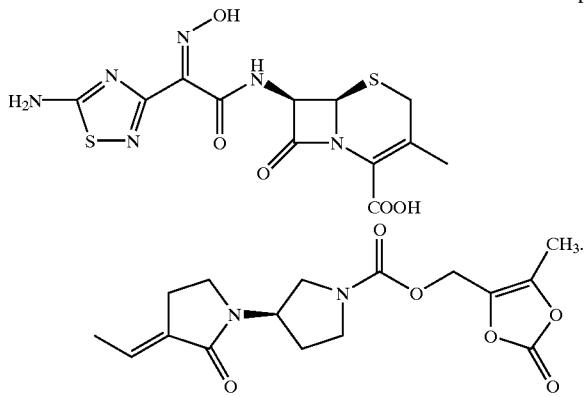

The compound of formula I is known and described in WO 99/65920. It is useful for the treatment and prophylaxis of infectious diseases, especially infectious diseases caused by bacterial pathogens, in particular, methicillin resistent *Staphylococcus aureus* (MRSA) and *Pseudomonas aeruginosa*.

a) oxidation of a 3-hydroxymethyl-cephem derivative to the corresponding 3-formyl-cephem derivative;
b) reaction of said compound with the ylide of 1-substituted 2-oxo-pyrrolidin compounds to 3-vinyl-pyrrolidone cephem derivatives;
c) deprotection and reaction with 5-amino-[1,2,4]thiadiazol-3-yl)-trityloxyimino-thioacetic acid S-benzothiazol-2-yl ester;
d) deprotection reactions; and
e) subsequent acylation reaction with carbonic acid 5-methyl-2-oxo-[1,3]dioxol-4-ylmethyl ester 4-nitro phenyl ester.

SUMMARY OF THE INVENTION

The present invention is a process for the preparation of a vinyl-pyrrolidinone cephalosporine derivative of formula I

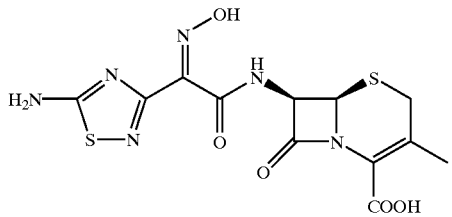

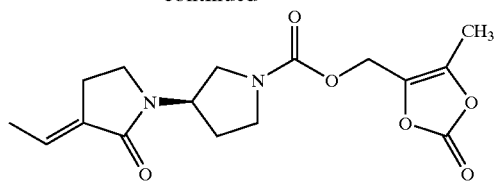

which process comprises:

acylating a compound of formula II

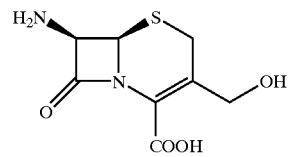

with a compound of formula III

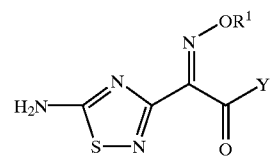

wherein $R^1$ is a hydroxy protecting group and Y is an activating group of formula Y1

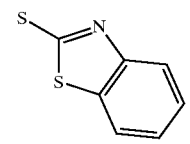

or of formula Y2

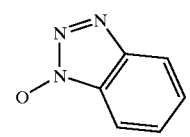

or of formula Y3,

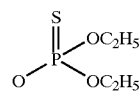

in the presence of a base, and protecting of the carboxylic acid group to form a compound of formula IV

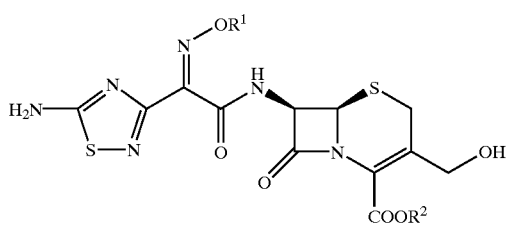

IV wherein R² is a carboxylic acid protecting group;
oxidizing the compound of formula IV with an inorganic hypohalite in the presence of 2,2,6,6-tetramethyl-1-piperidinyloxyl radical (TEMPO) or with manganese dioxide, to obtain the corresponding aldehyde derivative of formula V

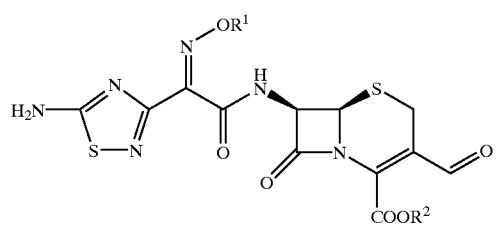

V reacting the compound of formula V with the ylide of the phosphonium salt of formula VI

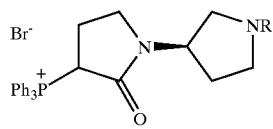

VI wherein Ph is phenyl and R is an amino protecting group or a group of formula A

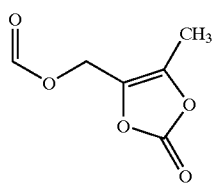

A to form a cephalosporine derivative of formula Ia

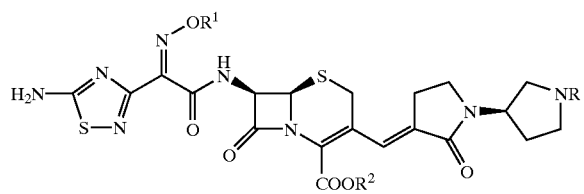

Ia and;
i) when R is an amino protecting group, cleaving off the protecting groups R¹, R² and R, and reacting the resulting unprotected compound with a compound of formula VII

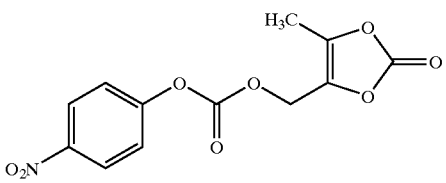

VII to obtain the vinyl-pyrrolidinone cephalosporine derivative of formula I; or ii) when R is a group of formula A, cleaving off the hydroxy and the carboxylic acid protecting groups R¹ and R² under acidic conditions to obtain the vinyl-pyrrolidinone cephalosporine derivative of formula I.

The present invention also provides a compound of formula IV

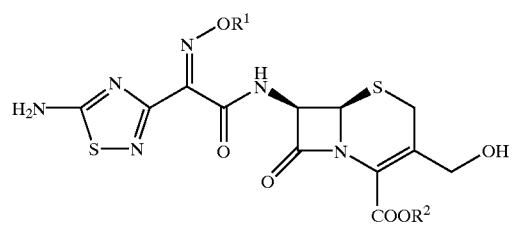

IV wherein R¹ is a hydroxy protecting group and R² is a carboxylic acid protecting group.

In addition, the present invention provides a compound of formula V

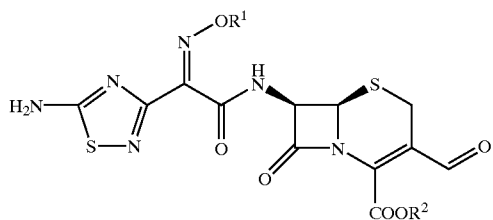

V wherein R¹ is a hydroxy protecting group and R² is a carboxylic acid protecting group.

Compounds IV and V are intermediates in the process of preparing the compound of formula I, in accordance with the present invention.

DETAILED DESCRIPTION OF THE INVENTION

It has been found that the compound of formula I can be manufactured in an improved way by the process of the present invention. The process of the present invention for the preparation of a vinyl-pyrrolidinone cephalosporine derivative of formula I

I

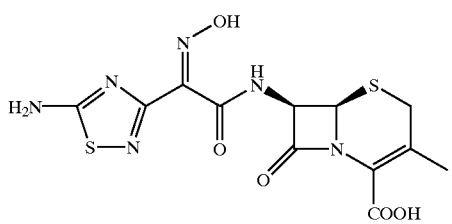

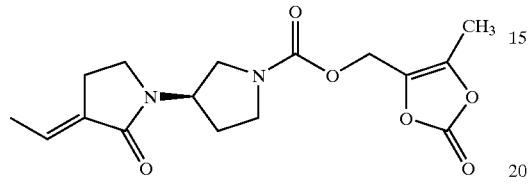

is characterized in that it comprises step (a) acylating a compound of formula II

II

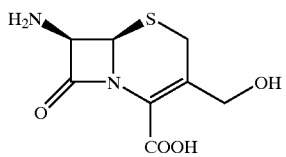

with a compound of formula III

III

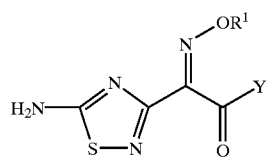

wherein R¹ is a hydroxy protecting group and Y is an activating group, as for example a group of formula Y1

Y1

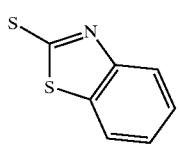

or of formula Y2

Y2

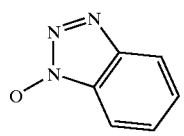

or of formula Y3,

Y3

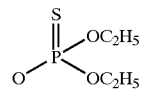

in the presence of a base, and subsequently protecting the carboxylic acid group to form the product of formula IV

IV

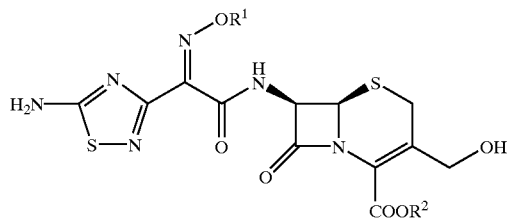

wherein R¹ is as defined above and R² is a carboxylic acid protecting group;

step (b) oxidizing the compound of formula IV with an inorganic hypohalite in the presence of 2,2,6,6-tetramethyl-1-piperidinyloxyl radical (TEMPO) or with manganese dioxide, to obtain the corresponding aldehyde derivative of formula V

V

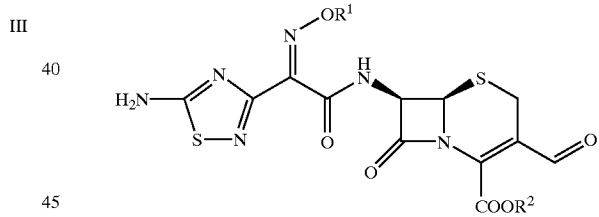

wherein R¹ and R² are as defined above;

step (c) reacting the compound of formula V with the ylide of the phosphonium salt of formula VI

VI

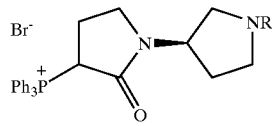

wherein Ph is phenyl and R is an amino protecting group or a group of formula A

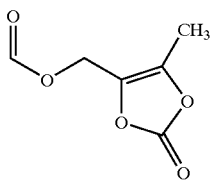

A to form the cephalosporine derivatives of formula Ia

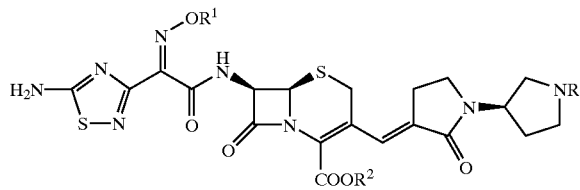

Ia wherein $R^1$, $R^2$ and R are as defined above; and step (d) i) when R is an amino protecting group, cleaving off the protecting groups $R^1$, $R^2$ and R, and reacting the unprotected compound subsequently with a compound of formula VII

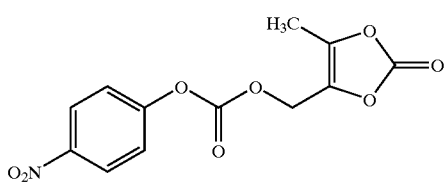

VII to obtain the vinyl-pyrrolidinone cephalosporine derivative of formula I; or ii) when R is a group of formula A, cleaving off the hydroxy and the carboxylic acid protecting groups $R^1$ and $R^2$ under acidic conditions to obtain the vinyl-pyrrolidinone cephalosporine derivative of formula I.

It has been surprisingly found, that due to the combination of process steps according to the invention, formula I is prepared by fewer steps and is obtained in higher yield, thereby decreasing production costs.

In the structural formulae presented herein a wedged bond (◂▬) denotes that the substituent is above the plane of the paper.

The term "hydroxy protecting group" as used herein denotes an alkyl group, a cycloalkyl group or an arylalkyl group. A preferred hydroxy protecting group is an arylalkyl group, especially preferred is a triphenylmethyl (trityl) group.

The term "activating group" as used herein denotes, for example, an activated ester such as a group of formula Y1 (mercaptobenzothiazole thioester) as described in EP 0849269 or of formula Y2 (1-hydroxybenzotriazole esters) or mixed anhydrides in analogy to those described in EP 0812846 such as Y3 (diethyl thiophosphoryl) or acid halides, in particular, acid chlorides in analogy to those described in J. Antibiot. (1984), 37(5), 557–71, which increase the reactivity of the carbon atom of the oxo group of the compound of formula III. The acylation of the compound of formula II with an activated compound of formula III results in a higher yield. A preferred activating group is the mercaptobenzothiazole thioester group.

The term "base" as used herein (step (a)) denotes a common base such as a tertiary amine, amidine base or a guanidine base.

The term "tertiary amine" as used herein denotes a group of formula $N(alkyl)_3$ in which the same or different alkyl groups are attached to the nitrogen atom. Examples are trimethyl amine, triethyl amine, dimethyl ethyl amine, methyl diethyl amine, tripropyl amine or tributyl amine.

The term "amidine base" as used herein denotes amidines or alkyl amidines in which 1, 2 or 3 hydrogen(s) are substituted by the same or different alkyl groups potentially also forming rings. Preferred amidine bases are 1,8-diazabicyclo[5.4.0]undec-7-en (DBU) and 1,8-diazabicyclo [4.3.0]non-5-en (DBN).

The term "guanidine base" as used herein denotes guanidine or alkyl guanidine in which 1, 2, 3, 4 or 5 hydrogen(s) (in the 1, 2 or 3-position) are substituted by the same or different alkyl group, potentially also forming rings. Preferred guanidine bases are alkyl guanidine bases such as 1,1,3,3-tetramethyl guanidine.

The term "alkyl" as used herein denotes a straight or branched chain hydrocarbon residue containing 1 to 7 carbon atoms, such as methyl, ethyl, propyl, isopropyl, butyl, isobutyl, tert.-butyl and the like.

The term "alkoxy" signifies an alkyl group as defined above which is bonded via an oxygen atom. Examples are methoxy, ethoxy, propyloxy, butoxy and the like.

By the term "cycloalkyl" as used herein denotes a 3–7 membered saturated carbocyclic moiety, e.g., cyclopropyl, cyclobutyl, cyclopentyl, cyclohexyl or cycloheptyl.

The term "aryl" as used herein denotes a phenyl group or a monosubstituted phenyl group which is substituted in the ortho-, meta- or para- position. Such substituents for the phenyl group are $C_{1-4}$-alkyl groups.

The term "aryloxy" signifies an aryl group as defined above which is bonded via an oxygen atom. Examples are phenyloxy and the like.

The term "arylalkyl" as used herein denotes a hydrocarbon group in which one or more alkyl hydrogen atoms are substituted by an aryl group such as trityl or benzhydryl.

The term "carboxylic acid protecting group" includes protecting groups which are usually used to replace a proton of the carboxyl group. Examples of such groups are described in Green T., Protective Groups in Organic Synthesis, Chapter 5, John Wiley and Sons, Inc. (1981), pp. 152–192. Known examples of such protecting groups are: benzhydryl, tert.-butyl, p-nitrobenzyl, p-methoxybenzyl, methoxymethyl and the like. Benzhydryl is a preferred carboxylic acid protecting group.

The term "amino protecting group" as used herein includes groups usually used to replace one proton or both protons of the amino group, such as those employed in peptide chemistry. Examples of such groups are described in Green T., Protective Groups in Organic Synthesis, Chapter 5, John Wiley and Sons, Inc. (1981), pp. 218–287, such as allyloxycarbonyl (ALLOC), an alkoxycarbonyl group such as tert.-butoxycarbonyl (t-BOC) and the like; a substituted alkoxycarbonyl group such as trichloroethoxycarbonyl; an optionally substituted aryloxycarbonyl group, for example, p-nitrobenzyloxycarbonyl or benzyloxycarbonyl; an arylalkyl group such as trityl (triphenylmethyl) or benzhydryl; an alkanoyl group such as formyl or acetyl; a halogen-alkanoyl group such as chloroacetyl, bromoacetyl, iodoacetyl or trifluoroacetyl; or a silyl protective group such as the trimethylsilyl group. Preferred amino protecting groups are tert.-butoxycarbonyl or allyloxycarbonyl.

The term "alkoxycarbonyl" denotes an alkoxy residue attached to a carbonyl group (C=O). Examples are methoxycarbonyl, ethoxycarbonyl, propoxycarbonyl, tert.-butoxycarbonyl and the like.

The term "aryloxycarbonyl" denotes an aryloxy residue attached to a carbonyl group (C=O). An example is benzyloxycarbonyl.

The term "acidic conditions" as used herein denotes a pH of the reaction mixture in the range of 1 to 7, preferably in the range of 2 to 6. An especially preferred pH is in the range of 3 to 6.

The term "inorganic hypohalites" as used herein denotes a compound such as sodium hypochlorite, potassium hypochlorite, calcium hypochlorite or sodium hypobromite. An especially preferred inorganic hypohalite is sodium hypochlorite.

In the first step of the process, a solution of a compound of formula II (preparation as described in DE 2128605) in an appropriate solvent is treated with a base, for example, a tertiary amine, an amidine or a guanidine base. A preferred base is an alkylated guanidine base. An especially preferred guanidine base is the commercially available 1,1,3,3-tetramethyl-guanidine. Appropriate solvents are polar aprotic solvents such as dimethylsulfoxid (DMSO), dimethylacetamide or N,N-dimethylformamid (DMF), preferably DMF. The solution is cooled to a temperature between about −20° C. and about +50° C., preferably to 0° C., and treated with a compound of formula III (preparation described for Y1 in EP 0 849 269; Y2: preparation in analogous manner as described in U.S. Pat. No. 5,672,711; Y3: preparation in analogous manner as described in EP 0 812 846) to obtain the acylation product. To protect the carboxylic acid group, the solution is subsequently diluted with water, washed with ethylacetate and the resulting aqueous layer is mixed with a halogenated hydrocarbon, such as $CH_2Cl_2$. The aqueous solution is cooled to a temperature between about −5° C. and about +35° C., preferably to 0° C. and reacted with diphenyldiazomethane (available from Sigma Aldrich) at a pH in the range of 1 to 9, preferably at a pH in the range of 1 to 7, more preferred at a pH in the range of 2 to 5, especially preferred at pH 3, to obtain the carboxylic acid protected compound of formula IV. After extraction, the compound of formula IV is isolated by rapid precipitation with a hydrocarbon such as pentane or hexane.

Also part of the present invention is a process for the preparation of a compound of formula IV

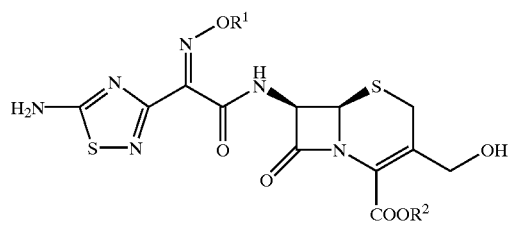

wherein $R^1$ is a hydroxy protecting group and $R^2$ is a carboxylic acid protecting group, which process is characterized in that it comprises step (a) acylating a compound of formula II

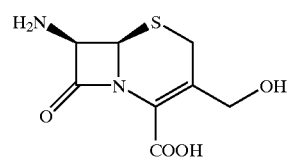

with a compound of formula III

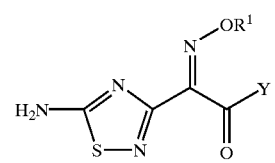

wherein $R^1$ is as defined above and Y is an activating group of formula Y1

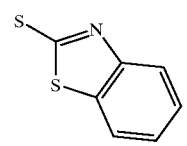

or of formula Y2

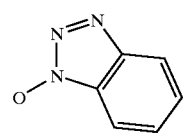

or of formula Y3,

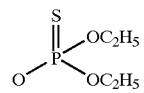

in the presence of a base, and subsequently protecting the carboxylic acid group to form the product of formula IV.

The compounds of formula IV are encompassed by the present invention. The compounds of formula IV may be used for the preparation of the vinyl-pyrrolidinone cephalosporine derivative of formula I

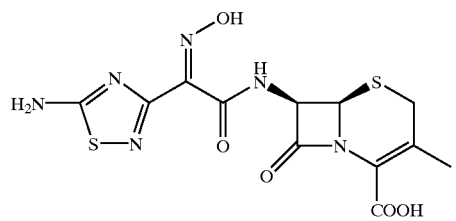

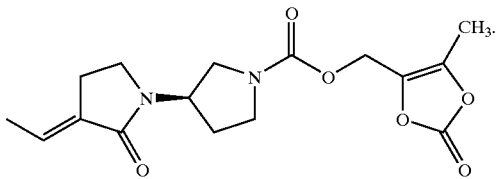

In the second step, the compound of formula IV is dissolved in an appropriate solvent and oxidized with a 20–100 molar excess (relative to the compound of formula IV) of manganese dioxide. Appropriate solvents are ethers such as tert.-butyl methyl ether (TBME) or tetrahydofurane (THF) or halogenated hydrocarbons such as $CH_2Cl_2$, preferably a mixture of such solvents. An especially preferred mixture is tetrahydofurane and dichloromethane.

In a preferred embodiment of the invention (step 2), the compound of formula V may also be obtained by the following way: A solution of the compound of formula IV in an appropriate solvent is treated with an inorganic salt such as KBr and a basic inorganic salt such as $NaHCO_3$ in water, cooled to a temperature between about −5° C. and about +35° C., preferably a temperature of 0° C., treated with 2,2,6,6-tetramethyl-1-piperidinyloxyl radical (TEMPO) (available from Fluka), and oxidized with an inorganic hypohalite such as sodium hypochlorite, potassium hypochlorite, calcium hypochlorite, sodium hypobromite, preferably sodium hypochlorite (J. Org. Chemistry, Vol 56, 1991, page 2416–2421). Appropriate solvents are ethers such as tert.-butyl methyl ether (TBME), esters such as ethyl acetate (AcOEt), hydrocarbons such as toluene or halogenated hydrocarbons, preferably $CH_2Cl_2$.

Also part of the present invention is a process for the preparation of a compound of formula V

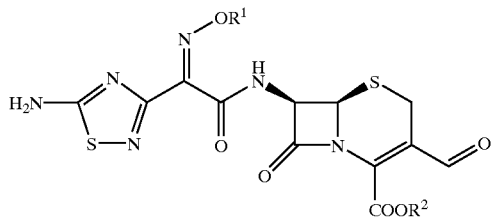

wherein $R^1$ is as defined above and $R^2$ is a carboxylic acid protecting group, which process is characterized in that it comprises oxidizing the compound of formula IV

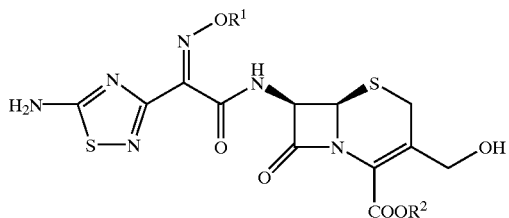

wherein $R^1$ and $R^2$ are as defined above, with an inorganic hypohalite in the presence of 2,2,6,6-tetramethyl-1-piperidinyloxyl radical (TEMPO) or with manganese dioxide to obtain the corresponding aldehyde derivative of formula V.

The compounds of formula V are encompassed by the present invention. The compounds of formula V may be used for the preparation of the vinyl-pyrrolidinone cephalosporine derivative of formula I.

In the third step, the phosphonium salt of formula VI (preparation see below) is dissolved in an appropriate solvent and reacted with a strong base to form the corresponding ylide. Appropriate bases are $t-C_4H_9OK$, $LiN(Si(CH_3)_3)_2$ or lithium diisopropylamide (LDA), preferably $t-C_4H_9OK$, which are dissolved in ethers, such as THF. Appropriate solvents are hydrocarbons such as toluene, halogenated hydrocarbons such as $CH_2Cl_2$, ethers such as THF or any combination of toluene, $CH_2Cl_2$ and THF. The resulting ylide in solution is reacted with a solution of the compound of formula V dissolved in an ether, such as THF, to form the cephalosporine derivatives of formula Ia. The reaction temperature is between about −120° C. and about +35° C., preferably between about −100° C. and about +30° C., most preferred at a temperature of −70° C.

Compounds of formula VI wherein R is an amino protecting group are prepared according to EP-A-0 849 269.

In the following the preparation of a compound of formula VI (wherein R is a group of formula A: compound VI-a) is described, which is used for the preparation of compounds of formula Ia ($3^{rd}$ step).

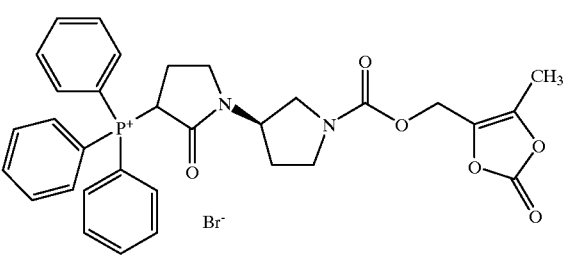

The compound of formula VI-a is prepared in that a mixture of (1R,3'R) and (1S,3'R)-(1'-allyloxycarbonyl-2-oxo-[1,3']bipyrrolidinyl-3-yl)-triphenyl-phosphonium bromide (prepared according to EP-A-0849269) is dissolved in an appropriate solvent and deprotected, for example, with bis-(triphenylphosphine)palladium dichloride, acetic acid and tributyltin hydride or equivalent methods known from the literature (e.g. J. March (1992), "Advanced Organic Chemistry: Reactions, Mechanisms and Structure", $4^{th}$ ed. John Wiley and Sons) to form the free bipyrrolidinyl compound. Appropriate solvents are hydrocarbons such as toluene or halogenated hydrocarbons, preferably $CH_2Cl_2$. The resulting intermediate is dissolved in hydrocarbons such as toluene or halogenated hydrocarbons such as $CH_2Cl_2$, and reacted with carbonic acid 5-methyl-2-oxo-[1,3]dioxol-4-ylmethyl ester 4-nitro phenyl ester (preparation described in U.S. Pat. No. 5,466,811) to yield to a mixture of (3R,3'R) and (3S,3'R) [1'-(5-methyl-2-oxo-[1,3]dioxol-4-ylmethoxycarbonyl)-2-oxo-[1,3']bipyrrolidinyl-3-yl]-triphenyl-phosphonium bromide (compound of formula VI-a).

The compound of formula VI-a is encompassed by the present invention. The compound of formula VI-a can be used for the preparation of the vinyl-pyrrolidinone cephalosporine derivative of formula I.

In the fourth step, the compound of formula Ia (when R is an amino protecting group) is deprotected with trialkylsilane, preferably triethylsilane in an amount between 1–5 equivalents (relative to compound of formula Ia) or by a combination of anisole in an amount between 1–50 equivalents (relative to compound of formula Ia), formic acid in an amount between 1–50 equivalents (relative to compound of formula Ia) and trifluoroacetic acid in an amount between 0.1–5 equivalents (relative to compound of formula Ia) in an appropriate solvent. Appropriate solvents are ethers such as THF, or halogenated hydrocarbons such as dichloromethane. The reaction is carried out at a temperature between about −30° C. and about 60° C., preferably at a reaction temperature of 30° C. The deprotected compound of formula Ia (when R is hydrogen) is subsequently reacted with 5-methyl-2-oxo-[1,3]dioxol-4-ylmethyl ester 4-nitro phenyl ester (preparation as described in U.S. Pat. No. 5,466,811) according the method as described in WO 99/65920 to obtain vinyl-pyrrolidinone cephalosporine derivative of formula I.

In an alternative fourth step, the hydroxy and carboxylic acid protecting groups of the compound of formula Ia (when R is a group of formula A) are cleaved under acidic conditions to obtain the vinyl-pyrrolidinone cephalosporine derivative of formula I. A mixture of the compound of formula Ia (when R is a group of formula A) and trialkylsilane, preferably triethylsilane, in an amount between 1–10 equivalents (relative to the compound of formula Ia), preferably in an amount between 4–6 equivalents, is dissolved in trifluoroacetic acid or a mixture of trifluoroacetic acid and a halogenated hydrocarbon such as dichloromethane in an amount of trifluoroacetic acid between 50–150 equivalents (relative to the compound of formula Ia), preferably in an amount between 85–115 equivalents. The reaction temperature is between about −5° C. and about 20° C., more preferably the reaction temperature is 0° C., and the compound of formula I is obtained after a reaction time which varies between 5 and 60 min.

In a preferred embodiment of the invention, the substituent $R^1$ is triphenylmethyl, $R^2$ is benzhydryl, tert.-butyl, p-nitrobenzyl, p-methoxybenzyl or methoxymethyl, R is tert.-butoxycarbonyl or allyloxycarbonyl and Y is a group Y1. In an especially preferred embodiment, $R^1$ is triphenylmethyl, $R^2$ is benzhydryl, R is tert.-butoxycarbonyl and Y is a group Y1.

In a further preferred embodiment of the process of the invention, $R^1$ is triphenylmethyl, $R^2$ is benzhydryl, tert.-butyl, p-nitrobenzyl, p-methoxybenzyl or methoxymethyl, R is a group of formula A and Y is a group Y1. Especially preferred is a process wherein $R^1$ is triphenylmethyl, $R^2$ is benzhydryl, R is a group of formula A and Y is a group Y1.

The vinyl-pyrrolidinone cephalosporine derivative of formula I obtained through the process as described in the invention may be used for the preparation of a pharmaceutical composition, for example, in the form of pharmaceutical preparations for parenteral administration. For this purpose the vinyl-pyrrolidinone cephalosporine derivative of formula I is preferably made into preparations as lyophilisates or dry powders for dilution with customary agents, such as water or isotonic common salt or carbohydrate (e.g. glucose) solution.

The pharmaceutical preparations may contain the vinyl-pyrrolidinone cephalosporine derivative of formula I for the prevention and treatment of infectious diseases in mammals, human and non-human. A daily dosage of about 10 mg to about 4000 mg, especially about 50 mg to about 3000 mg, is usual, with those of ordinary skill in the art appreciating that the dosage will depend also upon the age, conditions of the mammals, and the kind of diseases being prevented or treated. The daily dosage can be administered in a single dose or can be divided over several doses. An average single dose of about 50 mg, 100 mg, 250 mg, 500 mg, 1000 mg, and 2000 mg can be contemplated.

A further embodiment of the process of the invention is the preparation of a vinyl-pyrrolidinone cephalosporine derivative of formula Ia

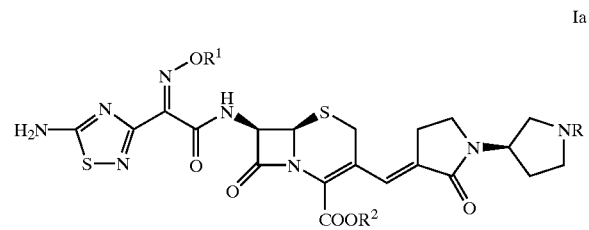

Ia wherein $R^1$ is a hydroxy protecting group, $R^2$ is a carboxylic acid protecting group and R is an amino protecting group which is characterized in that it comprises step (a) acylating a compound of formula II

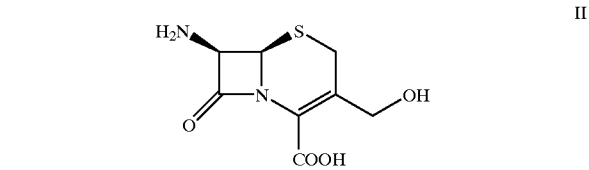

II with a compound of formula III

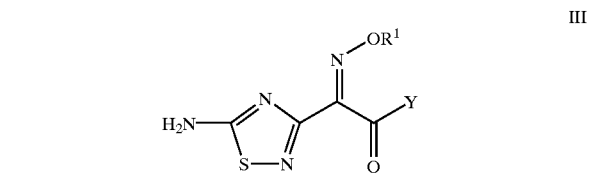

III wherein $R^1$ is a hydroxy protecting group and Y is an activating group, as for example, a group of formula Y1

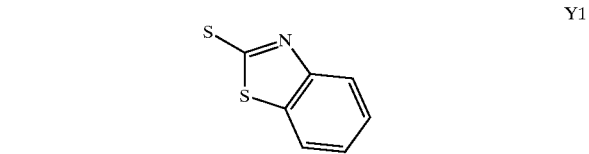

Y1 or of formula Y2

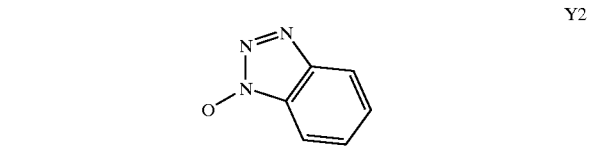

Y2 or of formula Y3,

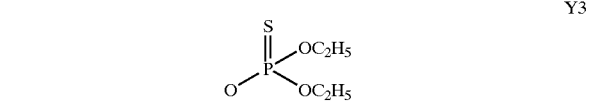

Y3 in the presence of a base, and subsequently protecting the carboxylic acid group
to form the product of formula IV

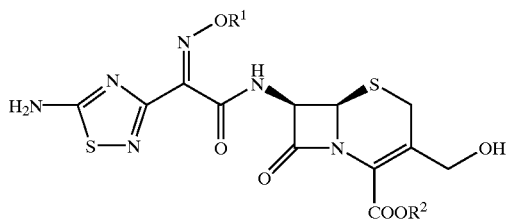

wherein $R^1$ and $R^2$ are as defined above;
step (b) oxidizing the compound of formula IV with an inorganic hypohalite in the presence of 2,2,6,6-tetramethyl-1-piperidinyloxyl radical (TEMPO) or with manganese dioxide to obtain the corresponding aldehyde derivative of formula V

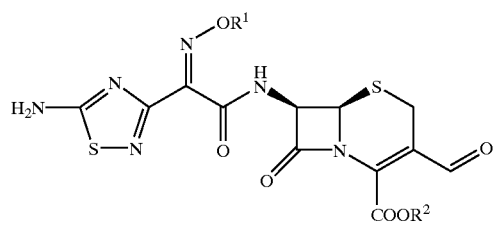

wherein $R^1$ and $R^2$ are as defined above;
step (c) reacting the compound of formula V with the ylide of the phosphonium salt of formula VI

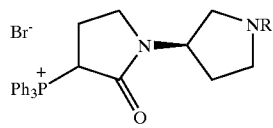

wherein Ph is phenyl and R is an amino protecting group or a group of formula A

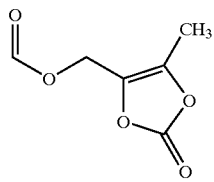

to form the cephalosporine derivatives of formula Ia.

In a preferred embodiment of the invention, the substituent $R^1$ is triphenylmethyl, $R^2$ is benzhydryl, tert.-butyl, p-nitrobenzyl, p-methoxybenzyl or methoxymethyl, R is tert.-butoxycarbonyl, allyloxycarbonyl or a group of formula A and Y is a group Y1. Especially preferred is that $R^1$ is triphenylmethyl, $R^2$ is benzhydryl, R is tert.-butoxycarbonyl or a group of formula A and Y is a group Y1.

The compounds of formula I prepared according to the invention may be used for the treatment and prophylaxis of infectious diseases, especially infectious diseases caused by bacterial pathogens, in particular, methicillin resistent *Staphylococcus aureus* (MRSA) and *Pseudomonas aeruginosa*.

In the following examples the abbreviations used have the following significations.

| | |
|---|---|
| MS | mass spectroscopy |
| NMR | nuclear magnetic resonance spectroscopy |
| IR | infrared spectroscopy |
| HPLC | high performance liquid chromatography |
| DMF | N,N-dimethylformamide |
| DMSO | dimethylsulfoxid |
| TEMPO | 2,2,6,6-tetramethyl-1-piperidinyloxyl radical |
| rt | room temperature |
| min | minute(s) |
| h | hour(s) |

All temperatures are given in degrees Celsius (° C.).

EXAMPLE 1

Step (a)

Preparation of 7-[2-(5-Amino-[1,2,4]thiadiazol-3-yl)-2-trityloxyimino-acetylamino]-3-hydroxymethyl-8-oxo-5-thia-1-aza-bicyclo[4.2.0]oct-2-ene-2-carboxylic Acid Benzhydryl Ester To a solution of 15.00 g of (6R,7R)-7-amino-3-hydroxymethyl-8-oxo-5-thia-1-aza-bicyclo[4.2.0.]oct-2-ene-2-carboxylic acid (preparation described in DE 2128605)) in 150 ml of N,N-dimethylformamide (DMF) was treated at 15° C. with 8.2 ml of 1,1,3,3-tetramethylguanidine (available from Fluka) and the suspension was stirred until a solution was obtained (10 min). This solution was treated at 0° C. with 38.95 g of (Z)-(5-amino-[1,2,4]thiadiazol-3-yl)-trityloxyimino-thioacetic acid S-benzothiazol-2-yl ester and stirring was continued at 0° C. for 4 h after which time HPLC indicated completion of the reaction. The solution was diluted with 300 ml of water and the aqueous layer was washed three times with 300 ml of ethyl acetate. The aqueous layer was cooled to 0° C., diluted with 350 ml of dichloromethane and with 160 ml of a 0.5 molar solution of diphenyldiazomethane (available from Sigma Aldrich) in dichloromethane, the pH was adjusted to 3 by addition of 1 N hydrochloric acid and stirring was continued at 0° C. for 2 h after which time HPLC indicated completion of the reaction. The layers were separated, the organic layer was washed twice with 300 ml of cold brine, dried over $MgSO_4$, filtered and the filtrate was diluted with 2700 ml of hexane leading to the precipitation of a gum. The solvent was decanted and the gum digested with 1250 ml of hexane. The suspension was filtered and the residue dried at 22° C./11 mbar for 16 h to give 47.68 g of the title compound as a pale yellow solid, m.p. 156° C. (dec.). IR (Nujol): 3429 m and 3240 m (OH, NH, $NH_2$), 1786 s, 1721 m, 1662 s (C=O). $^1$H-NMR ($d_6$-DMSO): 9.87 (d, J=8.8, 1H, NH); 8.13 (s, br. 2H, $NH_2$); 7.6–7.2 (m, 25H, H—ar.); 6.92 (s, 1H, $CH(Ph)_2$); 6.06 (dd, J=8.8 and 4.8, 1H, H—C(7)); 5.25 (d, J=4.8, 1H, H—C(6)); 5.15 (t, J=5.6, 1H, OH); 4.24 (d, J=5.6, 2H, $CH_2$—C(3)); 3.65 and 3.58 (d each, J=18.4 each, 2H, $CH_2$—S(5)). MS (CI): 809/100 (M+H$^+$).

EXAMPLE 2

Step (b): Oxidation of the Compound of Formula IV

Preparation of the 7-[2-(5-Amino-[1,2,4]thiadiazol-3-yl)-2-trityloxyimino-acetylamino]-3-formyl-8-oxo-5-thia-1-aza-bicyclo[4.2.0]oct-2-ene-2-carboxylic Acid Benzhydryl Ester 2.1 (via TEMPO, NaOCl): A suspension of 22.47 g 7-[2-(5-amino-[1,2,4]thiadiazol-3-yl)-2-trityloxyiminoacetylamino]-3-hydroxymethyl-8-oxo-5-thia-1-aza-bicyclo[4.2.0]oct-2-ene-2-carboxylic acid benzhydryl ester in 110 ml of dichloromethane was treated with a solution of 369 mg of KBr and 958 mg of $NaHCO_3$ in 70 ml of water, the mixture was cooled to 0° C. and treated with a solution of 391 mg of TEMPO (available from Fluka or as described in Synthesis, 1971, p. 190) in 2 ml of dichloromethane. The mixture was treated under vigorous stirring with 29 ml of NaOCl in water (9.93%) over 2 h and stirring was continued for 2 h after which time HPLC indicated completion of the reaction. The reaction mixture was filtered over Celite, the organic layer was washed with brine, treated with $MgSO_4$ and charcoal and filtered. The filtrate was stirred with 25 g of silica for 10 min, filtered and the filtrate was evaporated to dryness to give 16.61 g of the NMR-pure 7-[2-(5-amino-[1,2,4]thiadiazol-3-yl)-2-trityloxyimino-acetylamino]-3-formyl-8-oxo-5-thia-1-aza-bicyclo[4.2.0]oct-2-ene-2-carboxylic acid benzhydryl ester as a foam. IR (neat): 3432 w ($NH_2$, NH), 1800 m, 1783 m, 1670 m (C=O). $^1$H-NMR ($d_6$-DMSO): 9.98 (d, J=9.2, 1H, NH); 9.51 (s, 1H, CHO); 8.14 (s, br., 2H, $NH_2$); 7.55–7.25 (m, 25H, H—ar.); 7.10 (s, 1H, $CH(Ph)_2$); 6.30 (dd, J=9.2 and 5.6, 1H, H—C(7)); 5.41 (D, J=5.6, 1H, H—C(6)); 3.93 and 3.49 (each d, J=each 18, 2H, $H_2C(4)$). MS (CI): 807/100, M+H$^+$).

2.2 (via $MnO_2$): To a solution of 10.00 g (12.36 mMol) 7-[2-(5-amino-[1,2,4]thiadiazol-3-yl)-2-trityloxyimino-acetylamino]-3-hydroxymethyl-8-oxo-5-thia-1-aza-bicyclo[4.2.0]oct-2-ene-2-carboxylic acid benzhydryl ester in 100 ml tetrahydofurane and 100 ml dichloromethane is added in 13 portions in 15 min intervals 65 g manganese dioxide (0.75 Mol) with stirring. To the resulting suspension is added 10.0 g active coal and 500 ml ethyl acetate. The mixture is concentrated to a volume of 200 ml. To resulting suspension is added 100 ml n hexane and the mixture is purified by chromatography over 500 g silica gel using 1:2 mixture of n hexane: ethyl acetate as eluent. The product fraction are collected and evaporated to dryness under aspirator vacuum. The resulting foam is triturated with 30 ml t-butylmethyl ether to give 5.2 g of the title compound as a yellowish powder with identical analytical characteristics as in example 2.1.

EXAMPLE 3

Preparation of the Phosphonium Salt of Formula VI-a

Preparation of a Mixture of (3R,3'R) and (3S,3'R) [1'-(5-Methyl-2-oxo-[1,3]dioxol-4-ylmethoxycarbonyl)-2-oxo-[1,3']bipyrrolidinyl-3-yl]-triphenyl-phosphonium Bromide To a solution of a mixture of (1R,3'R) and (1S,3'R)-(1'-allyloxycarbonyl-2-oxo-[1,3']bipyrrolidinyl-3-yl)-triphenyl-phosphonium bromide (1:1) (10.0 g, 17.25 mMol) (prepared according to EP 1 067 131 A1) in 100 ml dichloromethane is added 0.364 g bis-(triphenylphosphine)palladium dichloride and 5.00 ml acetic acid. To the resulting mixture is added 10.00 ml tributyltin hydride and the mixture is stirred at room temperature for 45 min. The solids are removed by filtration and the mother liquor is poured into 1.50 l ethyl acetate. The resulting precipitate is collected by filtration and washed with ethyl acetate and diethyl ether and dried to constant weight under aspirator vacuum to yield 5.58 g of a white solid which is dissolved in 60 ml dichloromethane. To the resulting solution is added 2.90 g carbonic acid 5-methyl-2-oxo-[1,3]dioxol-4-ylmethyl ester 4-nitro phenyl ester (10 mMol) (available through the method as described in WO 99/65920) and the mixture is stirred at room temperature for 24 h. The solution is dropped into 1.00 l diethyl ether and the suspension is stirred for 10 min at room temperature. The solid is collected by filtration and dissolved in 60 ml water and 60 ml ethyl acetate. The phases are separated and the organic phase is extracted with water and the aqueous phases are backwashed with ethyl acetate. The combined aqueous phases are extracted twice with 100 ml dichloromethane. The combined dichloromethane phases are dried with magnesium sulfate and evaporated to dryness. The resulting solid is triturated with ethyl acetate collected by filtration washed with diethyl ether and dried to constant weight to yield 3.0 g of the title compound as a slightly beige powder. MS: M$^+$=571.1. 571.1. IR: 1817 (cyclic carbonate). $^1$H-NMR($d_6$-DMSO): 7.95–7.7 (m, 15H, 3×Ph); 5.59 (m, 1H, CO—CH); 4.89 (m, 2H, $OCH_2$); 4.30 (m, 1H, N—CH); 3.5–3.0 (m, 6H, 3×$CH_2$); (2.18 and each s together 3H, $CH_3$ isomers); 2.7–15 (m 4H, 2×$CH_2$).

EXAMPLE 4

Step (c): Reaction with the Phosphonium Salt of Formula VI

Preparation of 7-[2-(5-Amino-[1,2,4]thiadiazol-3-yl)-2-trityloxyimino-acetylamino]-3-[1'-(5-methyl-2-oxo-[1,3]dioxol-4-ylmethoxycarbonyl)-2-oxo-[1,3']bipyrrolidinyl-3-ylidenemethyl]-8-oxo-5-thia-1-aza-bicyclo[4.2.0]oct-2-ene-2-carboxylic Acid Benzhydryl Ester 4.1: To a solution of 1.22 g (1.875 mMol) mixture of (3R,3'R) and (3S,3'R) [1'-(5-methyl-2-oxo-[1,3]dioxol-4-ylmethoxycarbonyl)-2-oxo-[1,3']bipyrrolidinyl-3-yl]-triphenyl-phosphonium; bromide in 6.0 ml dichloromethane and 6.0 ml toluene is added a solution of 0.195 g (1.732 mMol) t-$C_4H_9OK$ in 6.00 ml tetrahydrofuran during 5 min at −30° C. and the mixture is stirred at this temperature for 45 min. To the resulting solution is added during 5 min a solution of 1.008 g (1.249 mMol) 7-[2-(5-Amino-[1,2,4]thiadiazol-3-yl)-2-trityloxyimino-acetylamino]-3-formyl-8-oxo-5-thia-1-aza-bicyclo[4.2.0]oct-ene-2-carboxylic acid benzhydryl ester in 3.0 ml tetrahydrofuran and the mixture is stirred for 45 min at −30° C. The mixture is quenched with 10% citric acid and the product is extracted with ethylacetate and purified by chromatography on silica gel using ethyl acetate:dichloromethane=4:1 to ethyl acetate as eluent. The product fraction are collected and evaporated to dryness whereby 0.6025 g of the title compound is obtained as a beige powder. MS (CI): M+=1099. IR: 1788 (beta-lactam carnolyl), 1818 (cyclic carbonate). $^1$H-NMR($d_6$-CDCl$_3$): 7.4–7.2 (m, 28H 5×Ph, $NH_2$, CH=C); 6.99 (s, 1H, $CHPh_2$); 6.73 (broadend d, 1H J=8.4, NH); 6.09 (dd, J=8.4; 4.8, $^1$H CH); 5.09 (d, J=8.4, 1H CH); 4.95–4.7 (m, 3H, CH, $CH_2$); 3.65–3.00 (m, 8H 4×$CH_2$); 2.6 (m, 1H CH); 2.35 (m, 1H, CH); 2.18 (s, 3H, $CH_3$); 2.1 (m, 1H CH); 1.95 (m, 1H, CH).

Preparation of (6R,7R)-7-[(Z)-2-(5-Amino-[1,2,4]thiadiazol-3-yl)-2-trityloxyimino-acetylamino]-3-[(E)-(R)-1'-tert.-butoxycarbonyl-2-oxo-[1,3']bipyrrolidinyl-3-ylidenemethyl]-8-oxo-5-thia-1-aza-bicyclo[4.2.0]oct-2-ene-2-carboxylic Acid 4.2 (small scale): To a solution of 2.45 g of (1'-tert.-butoxycarbonyl-2-oxo-[1,3']-bipyrrolidinyl-3-(R,S)-yl)-triphenyl-phosphonium bromide (preparation according EP 1 067 131 A1) in 6 ml of dichloromethane and 15 ml of toluene was added at −78° C. a solution of 432 mg of t-$C_4H_9OK$ in 6 ml of THF over 10 min and stirring was continued at −78° C. for 10 min. The solution was treated at −78° C. with a solution of 3.50 g 7-[2-(5-amino-[1,2,4]thiadiazol-3-yl)-2-trityloxyimino-acetylamino]-3-formyl-8-oxo-5-thia-1-aza-bicyclo[4.2.0]oct-2-ene-2-carboxylic acid benzhydryl ester in 6 ml of THF over 15 min and stirring was continued at −78° C. for 6 h and at −50° C. for 1 h after which time HPLC showed almost completion of the reaction. The reaction was quenched with a solution of 0.95 g of citric acid in 9 ml of water followed by addition of 12 ml of ethyl acetate, the organic layer was washed with $NaHCO_3$ and brine, dried over $MgSO_4$, filtered and the filtrate was evaporated. The residue was chromatographed on silica with ethyl acetate/hexane 10:1 to give 1.82 g of the title compound as a foam. IR (Nujol): 3450 m (NH2, NH), 1779 s, 1724 s, 1678 s, 1653 s (C═O). 1H-NMR ($d_6$-DMSO): 9.93 (d, J=8.8, 1H, NH); 8.13 (s, br., 2H, $NH_2$); 7.6–7.3 (m, 26H, H—ar., HC—C(3)); 6.96 (s, 1H, CH(Ph)$_2$); 6.15 (dd, J=8.8 and 4.8, 1H, H—C(7)); 5.33 (d, J=4.8, 1H, H—C(6)); 4.59 (m, 1H, CH—N)); 3.91, 3.85 (d each, J=18 each, 2H, $CH_2$—S(5)); 3,5–3,3 and 2.9 and 2.7 and 2.0 (m each, 6H and 1H and 1H and 2H, 5×$CH_2$); 1.41 (s, 9H, $(CH_3)_3C$). MS (CI): 1044/100 (M+H$^+$).

4.2 (large scale): To a solution of 14.64 g of (1'-tert.-butoxycarbonyl-2-oxo-[1,3']-(R)-bipyrrolidinyl-3-(R,S)-yl)-triphenyl-phosphonium bromide (preparation according EP 1 067 131 A1) in 30 ml of dichloromethane and 75 ml of toluene was added at −78° a solution of 2.581 g of t-$C_4H_9$OK in 30 ml of THF over 30 min and stirring was continued at −78° for 30 min. The solution was treated at −78° with a solution of 19.00 g of 7-[2-(5-amino-[1,2,4]thiadiazol-3-yl)-2-trityloxyimino-acetylamino]-3-formyl-8-oxo-5-thia-1-aza-bicyclo[4.2.0]oct-2-ene-2-carboxylic acid benzhydryl ester in 30 ml of THF over 20 min and stirring was continued at −78° for 3 h after which time HPLC showed almost completion of the reaction. The reaction was quenched at −20° with a solution of 16 g of citric acid in 140 ml of water and the aqueous solution was washed twice with 200 ml of ethyl acetate. The organic layer was washed with $NaHCO_3$ and brine, dried over $MgSO_4$, filtered and the filtrate was evaporated to dryness. The residue was digested twice with 125 ml of ethanol, the suspension was filtered and the residue was dried to give 18.97 g of the crude product as a brown solid. The product can be further purified by crystallization from dichloromethane/t-butyl methyl ether or by chromatography on silica with ethyl acetate/hexane 10:1. Identical IR, NMR and MS characteristics as in example 4.2 (small scale).

EXAMPLE 5

Step (d) i): Deprotection Reaction when R is an Amino Protecting Group

Preparation of (6R,7R)-7-[(Z)-2-(5-Amino-[1,2,4]thiadiazol-3-yl)-2-hydroxyimino-acetylamino]-8-oxo-3-[(E)-(R)-2-oxo-[1,3']bipyrrolidinyl-3-ylidenemethyl]-5-thia-1-aza-bicyclo[4.2.0]oct-2-ene-2-carboxylic Acid 5.1 (small scale): A suspension of 149 mg of (6R,7R)-7-[(Z)-2-(5-amino-[1,2,4]thiadiazol-3-yl)-2-trityloxyimino-acetylamino]-3-[(E)-(R)-1'-tert.-butoxycarbonyl-2-oxo-[1,3']bipyrrolidinyl-3-ylidene-methyl]-8-oxo-5-thia-1-aza-bicyclo[4.2.0]oct-2-ene-2-carboxylic acid and 0.24 ml of methyl phenyl ether in 0.8 ml of formic acid was treated with 0.26 ml of dichloromethane containing 2% of trifluoroacetic acid and the solution was heated to 30° C. for 3 h after which time HPLC indicated completion of the reaction. The mixture was diluted with 3 ml of toluene and evaporated to dryness. The residue was diluted with 2 ml of methanol and 6 ml of water, the pH was adjusted to 9 by adding diluted ammonia and the aqueous layer was washed three times with ethyl acetate. The pH of the aqueous layer was adjusted to 3 by adding diluted hydrochloric acid and the solution was evaporated to dryness. The residue was digested with t-butyl methyl ether, filtered and the residue dried to give 73 mg of the NMR-pure title compound as a pale yellow solid. $^1$H-NMR ($d_6$-DMSO+1 equivalent of $CF_3COOH$, only some selected signals given): 7.26 (s, 1H, CH—C(3)); 5.88 (d, J=4.8, 1H, H—C(7)); 5.18 (d, J=4.8, 1H, H—C(6)); 3.88 and 3.86 (d each, J=18 each, 2H, $CH_2$—S(5)); 3.5–2.8 (m, 8H, 4×$CH_2$); 2.2–2.0 (m, 2H, $CH_2$).

5.2 (large scale): A suspension of 5.785 g of (6R,7R)-7-[(Z)-2-(5-amino-[1,2,4]thiadiazol-3-yl)-2-trityloxyimino-acetylamino]-3-[(E)-(R)-1'-tert.-butoxycarbonyl-2-oxo-[1,3']bipyrrolidinyl-3-ylidene-methyl]-8-oxo-5-thia-1-aza-bicyclo[4.2.0]oct-2-ene-2-carboxylic acid and 1.69 ml of triethylsilane in 25 ml of dichloromethane was treated at −15° with 7.21 ml of trifluoroacetic acid and the solution was heated to 30° for 30 min after which time HPLC indicated completion of the reaction. The mixture was evaporated to dryness, the residue was digested with 60 ml of ethyl acetate, the suspension was filtered and the residue dried to give 3.43 g of the crude title compound as a brown solid, containing about 1.4 equivalents of ethylacetate. $^1$H-NMR ($d_6$-DMSO): 13.9 (s, br., 1H, COOH); 11.94 (s, 1H, OH); 9.50 (d, J=8.4, 1H, NH—C(7)); 8.96 (s, br., 2H, $NH_2$); 8.07 (s, br., 2H, $NH_2$); 7.26 (s, br., 1H, CH—C(3)); 5.88 (dd, J=8.4 and 4.9, 1H, H—C(7)); 5.18 (d, J=4.9, 1H, H—C(6)); 4.64 (m, 1H); 3.87 (s, br., 2H $H_2C(4)$); 3.9–2.7 (m, 8H); 2.2–2.0 (m, 2H).

EXAMPLE 6

Step (d) ii): Deprotection Reaction when R is a Group of Formula A

Preparation of (6R,7R)-7-[(Z)-2-(5-Amino-[1,2,4]thiadiazol-3-yl)-2-hydroxyimino-acetylamino]-3-[(E)-(R)-1'-(5-methyl-2-oxo-[1,3]dioxol-4-ylmethoxycarbonyl)-2-oxo-[1,3']bipyrrolidinyl-3-ylidenemethyl]-8-oxo-5-thia-1-aza-bicyclo[4.2.0]oct-2-ene-2-carboxylic Acid A mixture of 40 mg 7-[2-(5-amino-[1,2,4]thiadiazol-3-yl)-2-trityloxyimino-acetylamino]-3-[1'-(5-methyl-2-oxo-[1,3]dioxol-4-ylmethoxycarbonyl)-2-oxo-[1,3']bipyrrolidinyl-3-ylidenemethyl]-8-oxo-5-thia-1-aza-bicyclo[4.2.0]oct-2-ene-2-carboxylic acid benzhydryl ester and 20 mg triethylsilane is dissolved in 0.30 ml trifluoroacetic acid. The resulting solution is stirred at 0° C. for 15 min. The solvent is evaporated under aspirator vacuum and the residue is triturated with diethyl ether. The solid is collected by filtration and washed with diethyl ether to yield 23 mg of the title compound as beige powder. MS: M−H=689.3. $^1$H-NMR ($d_6$-DMSO): 13.8 (s, 1H, COOH); 11.9 (s, 1H, OH); 9.45 (d, J=8.4, 1H, NH); 8.05 (s, 2H, $NH_2$); 7.31(s, 1H, HC═C); 5.86 (dd, J=8.4; 4.8, 1H CH); 5.17 (d, J=8.4, 1H CH); 4.61 (m, 1H CH); 3.85 (m, 2H $CH_2$); 3.55–3.35 (m, 6H 3×$CH_2$); 3.1 (m, 1H); 2.9 (m, 1H); 2.15 (s, 3H, $CH_3$); 2.05 (m, 2H $CH_2$).

What is claimed is:

1. A process for the preparation of a vinyl-pyrrolidinone cephalosporine derivative of formula I

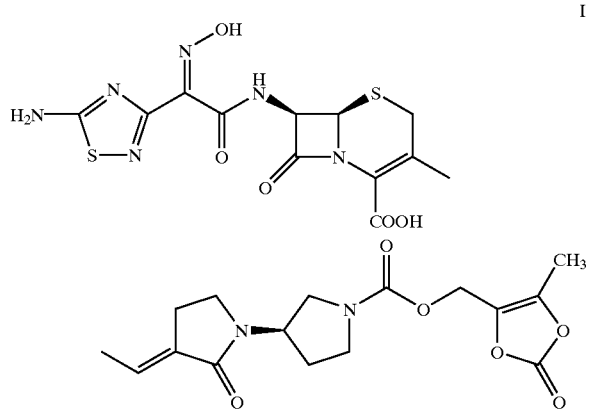

which process comprises:
(a) acylating a compound of formula II

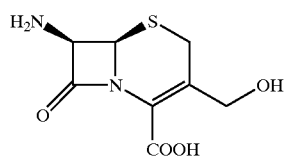

with a compound of formula III

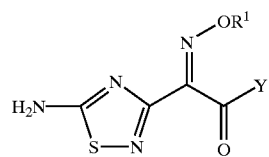

wherein $R^1$ is a hydroxy protecting group and Y is an activating group of formula Y1

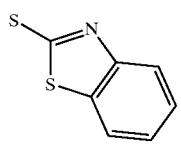

or of formula Y2

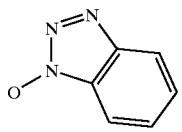

or of formula Y3,

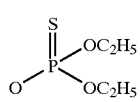

in the presence of a base, and protecting the carboxylic acid group to form a compound of formula IV

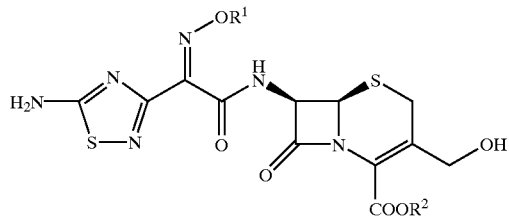

wherein $R^2$ is a carboxylic acid protecting group;
(b) oxidizing the compound of formula IV with an inorganic hypohalite in the presence of 2,2,6,6 tetramethyl-1-piperidinyloxyl radical (TEMPO) or with manganese dioxide, to obtain the corresponding aldehyde derivative of formula V

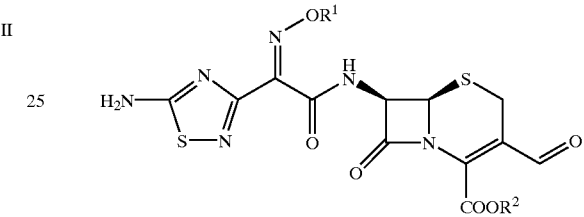

(c) reacting the compound of formula V with the ylide of the phosphonium salt of formula VI

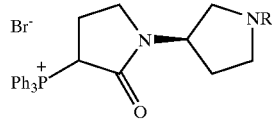

wherein Ph is phenyl and R is an amino protecting group or a group of formula A

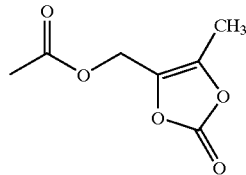

to form a cephalosporine derivative of formula Ia

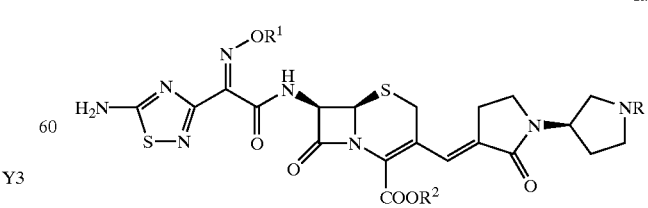

and;
(d) i) when R is an amino protecting group, cleaving off the protecting groups $R^1$, $R^2$ and R, and reacting the resulting unprotected compound with a compound of formula VII

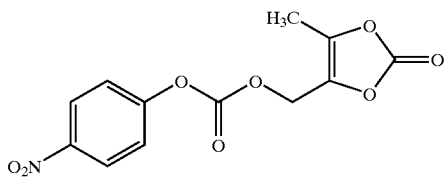

to obtain the vinyl-pyrrolidinone cephalosporine derivative of formula I; or ii) when R is a group of formula A, cleaving off the hydroxy and the carboxylic acid protecting groups R¹ and R² under acidic conditions to obtain the vinyl-pyrrolidinone cephalosporine derivative of formula I.

2. A process for the preparation of a compound of formula IV

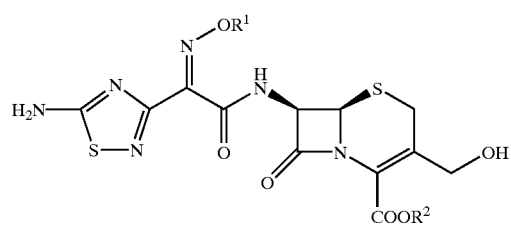

wherein R¹ is a hydroxy protecting group and R² is a carboxylic acid protecting group, which process comprises:

(a) acylating a compound of formula II

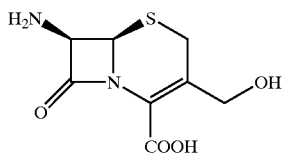

with a compound of formula III

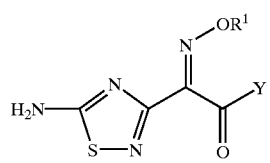

wherein R¹ is a hydroxy protecting group and Y is an activating group of formula Y1

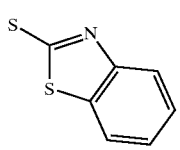

or of formula Y2

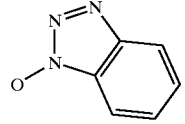

or of formula Y3, $$\underset{O}{\overset{S}{\underset{\|}{P}}}\underset{OC_2H_5}{\overset{OC_2H_5}{<}}$$

Y3 in the presence of a base, and subsequently protecting the carboxylic acid group to form the compound of formula IV.

3. A process for the preparation of a compound of formula V

V wherein R¹ is a hydroxy protecting group and R² is a carboxylic acid protecting group, which process comprises oxidizing the compound of formula IV

IV with an inorganic hypohalite in the presence of 2,2,6,6-tetramethyl-1-piperidinyloxyl radical (TEMPO) or with manganese dioxide, to obtain the corresponding aldehyde derivative of formula V.

4. A process as claimed in claim 1 wherein R¹ is triphenylmethyl, R² is benzhydryl, tert.-butyl, p-nitrobenzyl, p-methoxybenzyl or methoxymethyl, R is tert.-butoxycarbonyl or allyloxycarbonyl and Y is Y1.

5. A process as claimed in claim 1 wherein R² is benzhydryl and R is tert.-butoxycarbonyl.

6. A process as claimed in claim 1 wherein R¹ is triphenylmethyl, R² is benzhydryl, tert.-butyl, p-nitrobenzyl, p-methoxybenzyl or methoxymethyl, R is a group of formula A and Y is Y1.

7. A process as claimed in claim 6 wherein R² is benzhydryl.

8. A process as claimed in claim 1 wherein the acylation reaction in step (a) is carried out in the presence of an alkylated guanidine base in a polar aprotic solvent at a temperature between about −20° C. and about +50° C., and the protection of the carboxylic acid group is carried out at a temperature between about −5° C. and about +35° C. at a pH in the range of 1 to 9.

9. A process as claimed in claim 1 wherein the oxidation reaction in step (b) is carried out with a 20–100 molar excess, relative to the compound of formula IV, of manganese dioxide in at least one ether, at least one halogenated hydrocarbon or a mixture thereof.

10. A process as claimed in claim 1 wherein the oxidation reaction in step (b) is carried out with sodium hypochlorite, potassium hypochlorite, calcium hypochlorite or sodium hypobromite in the presence of 2,2,6,6-tetramethyl-1-piperidinyloxyl radical (TEMPO) at a temperature between about −5° C. and about +35° C. in at least one ether,ester, hydrocarbon orhalogenated hydrocarbon.

11. A process as claimed in claim 1, wherein the ylide of the phosphonium salt of formula VI of step (c) is formed by reacting the phosphonium salt of formula VI in at least one hydrocarbon, halogenated hydrocarbon or a mixture thereof with t-$C_4H_9OK$, $LiN(Si(CH_3)_3)_2$ or lithium diisopropylamide at a reaction temperature between about −100° C. and about +35° C., and said ylide is reacted with a compound of formula V at a reaction temperature between about −120° C. and about +35° C., to form the cephalosporine derivative of formula Ia.

12. A process as claimed in claim 1, wherein the deprotection reaction in step (d) i) is carried out with a combination of from 1–50 equivalents anisole, from 1–50 equivalents formic acid and from 0.1–5 equivalents trifluoroacetic acid or from 1–5 equivalents trialkylsilane in at least one ether or at least one halogenated hydrocarbon at a reaction temperature between about −30° C. and about 60° C.

13. A process as claimed in claim 1, wherein the cleaving of the hydroxy and carboxylic acid protecting groups in step (d) ii) is carried out with from 1–10 equivalents trialkylsilane and from 50–150 equivalents trifluoroacetic, or from 1–10 equivalents trialkylsilane and a mixture of from 50–150 equivalents trifluoroacetic acid and a halogenated hydrocarbon at a reaction temperature from about −5° C. to about 20° C.

14. A compound of formula IV

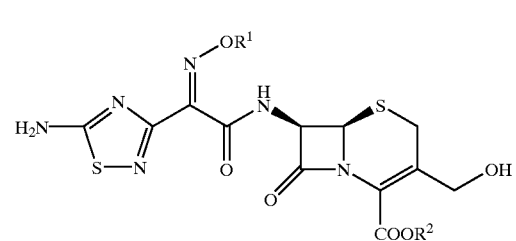

IV wherein $R^1$ is a hydroxy protecting group and $R^2$ is a carboxylic acid protecting group.

15. A compound of formula V

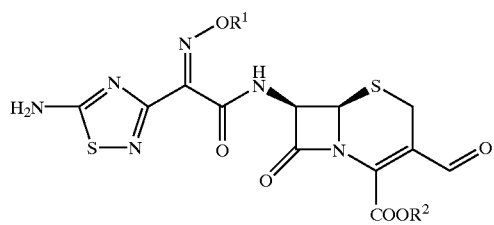

V wherein $R^1$ is a hydroxy protecting group and $R^2$ is a carboxylic acid protecting group.

16. A mixture comprising (3R,3'R) [1'-(5-methyl-2-oxo-[1,3]dioxol-4-ylmethoxycarbonyl)-2-oxo-[1,3']bipyrrolidinyl-3-yl]-triphenyl-phosphonium bromide and (3S,3'R) [1'-(5-methyl-2-oxo-[1,3]dioxol-4-ylmethoxycarbonyl)-2-oxo-[1,3']bipyrrolidinyl-3-yl]-triphenyl-phosphonium bromide.

* * * * *